United States Patent [19]

Durie et al.

[11] 4,035,155
[45] July 12, 1977

[54] METHOD OF HIGH SPEED SCINTILLATION AUTORADIOGRAPHY

[75] Inventors: Brian G. M. Durie; Sydney E. Salmon, both of Tucson, Ariz.

[73] Assignee: University Patents, Inc., Stamford, Conn.

[21] Appl. No.: 627,218

[22] Filed: Oct. 30, 1975

[51] Int. Cl.$^2$ .................. G01N 23/00; G01N 23/04
[52] U.S. Cl. .......................... 23/230.3; 23/230 B; 195/103.5 R; 250/304; 424/1; 424/1.5
[58] Field of Search ........... 23/230 B, 230.3, 230.6; 424/1; 195/103.5 R; 250/303, 304, 308, 320

[56] References Cited
PUBLICATIONS

Chemical Abstracts, 68: 833c (1968).
Chemical Abstracts, 69: 83361s–t (1968).
Chemical Abstracts, 79: 112082r (1973).
Chemical Abstracts, 81: 74375v (1974).

*Primary Examiner*—Morris O. Wolk
*Assistant Examiner*—Sidney Marantz
*Attorney, Agent, or Firm*—Mason, Kolehmainen, Rathburn & Wyss

[57] ABSTRACT

Autoradiography using high specific activity tritiated thymidine (40-60 curies/millimole) and nuclear track emulsion impregnated with a liquid scintillator provides a very rapid method to determine labelling index and growth fraction of cell suspensions. Low temperature (−20° to −85° C) emulsion exposure for 20 – 60 minutes is sufficient for excellent labelling, thus allowing rapid clinical decision making. Exposure times for research techniques requiring very low energy labelling can be considerably shortened, e.g., from 6 months to 2 weeks or less. This technique therefore has broad applicability to biology and medicine.

5 Claims, 2 Drawing Figures

METHOD OF HIGH SPEED SCINTILLATION AUTORADIOGRAPHY

This invention relates to a method of high speed autoradiography. More particularly, it relates to a method of autoradiography in which critical biological substances such as DNA, RNA or hormones are radioactively labeled with tritium (H3).

BACKGROUND OF THE INVENTION

Autoradiography is a technique for tracking the movement and location in living cells of a component or building block, which is labeled with a radioactive isotope, of a compound which is important to cell life and function such as DNA, RNA, or an enzyme. The component or building block which is labeled with the radioactive isotope is, during the usual function of the cell, incorporated into an essential cell constituent such as RNA, DNA or an enzyme. The rate of incorporation of the labeled building block or component into the cell is a measure of the activity of that cell which provides useful physiological information which is valuable in clinical research and medicine.

Among the important cell constituents which can be followed in this fashion are DNA and RNA. The rate of production of DNA or RNA in a living cell is a measure of the physiological activity of that cell and provides data which may indicate whether that cell may be normal or abnormal. For example, cells of malignant tissues have abnormal growth kinetics and may have disturbed DNA and/or RNA turnover. By measuring the production of DNA or RNA through a radioactive isotope-labeled component of DNA or RNA such as tritiated thymidine or tritiated uridine, it is possible to determine the activity of the cell and thus get useful information which will aid in determining whether the cell is malignant or normal and, if malignant, whether it would be subject to chemotherapeutic treatment.

Autoradiography enables a physiologist to determine, for example, which cells of a tissue are synthesizing DNA or RNA at a normal or rapid rate and how much of these materials are produced per cell. From such data, it is possible to determine whether the tissue containing the cells under investigation may be susceptible to chemotherapy which interferes with cell growth.

In the practice of autoradiography, tissues under examination are broken down into a suspension of living cells. The suspension of cells under evaluation is incubated with the tritiated isotope, such as tritiated thymidine or tritiated uridine. The synthesis of DNA or RNA by those cells can be evaluated in terms of the rate and amount of isotope incorporated. The DNA or RNA which contains the radioactive thymidine or uridine are thus labeled with a radioactive isotope (tritium) and can be traced or tracked through normal physiological processes by radioactive tracking procedures. Through such techniques, it is possible to obtain accurate data relative to the production of DNA or RNA by the cells under investigation. The same techniques can be used in studying the kinetics of other cell constituents.

SUMMARY OF THE INVENTION

This invention relates to a high speed method of autoradiography which allows the physiologist to obtain data on the growth or production of DNA or other essential physiological components of living cells, such as RNA and hormones or enzymes in a much shorter period of time than has heretofore been possible. By this rapid technique, it is possible to examine a patient, determine the rate of cell function in a specific tissue, and recommend chemotherapeutic treatment, all in the same day. This is particularly important in patients suffering from malignancies.

The high speed autoradiography development which constitutes this invention involves the use of tritiated (radioactive) compounds such as thymidine or uridine, the tritium being of high specific activity (in the range of 40–60 or more curies per millimole), combined with a liquid scintillator medium, the effect of which is enhanced at low temperature (−20° to −80° C). By this technique, it is possible to get excellent labelling with tritium compounds in an hour or less, thus allowing rapid clinical evaluation and therapy decision making. This invention has broad applicability to biology and medicine.

GENERAL DESCRIPTION OF INVENTION

Conventional autoradiography for determination of labelling index and growth fraction requires at least six days to complete. By using high specific activity tritiated thymidine (40–60 curies/millimole), a liquid scintillator and emulsion exposure at low temperature (−20° to −85° C), we have developed a method of very high speed scintillation autoradiography. With these techniques fresh blood, bone marrow and tumor cell samples can be processed to provide thymidine labelling results within five hours.

The activation of silver crystals in the photographic emulsion used in autoradiography is dependent upon the number and energy of the beta emissions penetrating the emulsion. With standard ARG the level of beta emission is relatively low. However, with an isotope of very high specific activity (such as the tritiated thymidine used in our studies), there are many more beta emissions per molecule of incorporated isotope. When, in addition, the emulsion is impregnated with scintillator, photons are released as the electrons (beta particles) pass through the scintillator, and this activates even more silver crystals in the emulsion. Increased sensitivity is accompanied by a slight increase in the scatter of emissions. However, in practice this scatter is minimal and does not affect interpretation of the data.

Heparinized cell suspensions are incubated for one hour with high specific activity tritiated thymidine. Preferably 5.0 micro-curies/cc are added to cell suspensions prepared at $0.5 - 1.0 \times 10^6$ cells/cc. Cytocentrifuge smears are then made on gelatin-coated slides and fixed with methanol. In the dark room the slides are first dipped for 10 seconds into nuclear track emulsion (NTB 3, Eastman Kodak Co.) at 42° C. After drying for approximately 1 hour, slides are next dipped for 10 seconds into the scintillator solution. The preferred scintillator solution comprises a combination of 2,5-diphenyloxazole (PPO) and 1,4-bis-(4-methyl-5-phenyloxazol-2-yl)benzene (dimethyl POPOP) dissolved in dioxane. The scintillator-impregnated emulsion is exposed in the dark for 20–60 minutes. Slides are then developed at 17° C in the usual way. The cytocentrifuge smears are stained directly through the emulsion with buffered Giemsa stains.

The various steps in the eventually successful procedure were studied and analyzed separately. Lymphocytes stimulated in vitro with phytohemagglutinin were used as a reliable source of highly labelled cells.

Figure 1:
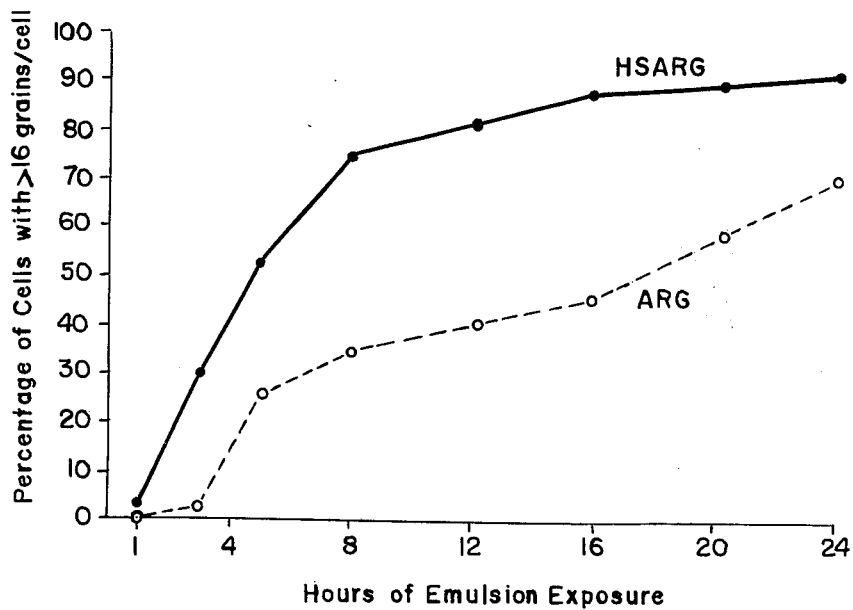
FIGS. 1 and 2 are graphs illustrating the activity of cells investigated by high speed autoradiography (HSARG), as disclosed in this application, compared to the activity of cells in conventional autoradiography (ARG). The percentages of labeled cells causing deposit of silver grains are plotted against exposure times in each graph. It is seen that HSARG produces useful data much more rapidly than ARG.
Figure 2:
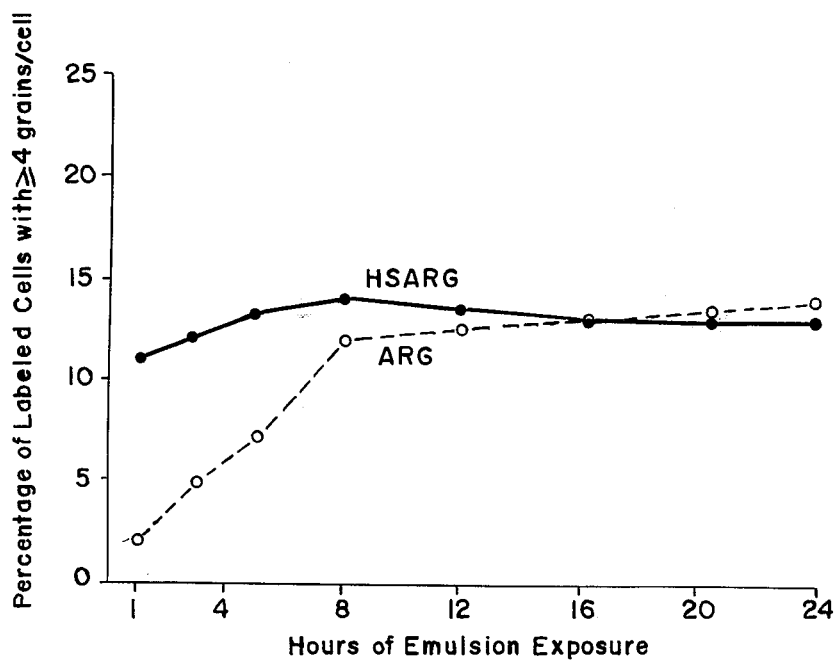

Using high specific activity tritiated thymidine, multiple experiments were carried out exposing slides for 1 - 24 hours with and without coating with scintillator solution. FIG. 1 illustrates the effect of scintillator. Close to maximal labelling was reached in 5 hours and within only one hour approximately 75% of final labelling was achieved. Duplicate and triplicate samples showed consistently more rapid labelling with the scintillator solution (P<0.05 for the 1 and 5 hour time points). In additional studies, emulsion exposure was extended to 6 days and the final labelling compared with labelling using lower specific activity tritiated thymidine (2 curies/millimole). The final labelling was detected eventually in the same number of cells identified considerably earlier using the rapid technique. Cell viability was checked post incubation with isotope and found to be consistently greater than 95%.

The number of grains/cell was greatly enhanced by use of the scintillator. With high speed autoradiography 50% of cells had greater than 15 grains per nucleus at five hours. Background labelling was remarkably low even allowing exposure for six days. For time points up to 24 hours the mean background grain count was 38 grains per hundred cells with a maximum of 65 grains per hundred. From the Poisson probability law there is only a 0.05% chance that background could account for greater than 4 grains per cell. Therefore five or more grains per cell was interpreted as definite labelling in this procedure.

Temperature is known to significantly affect fluorography on thin layer chromatography with tritium compounds. It has been suggested that at low temperatures the vibrational freedom of molecules is "frozen in" and thus energy goes into photon emission which otherwise would be lost in random motion. We thus studied the effect of temperature upon high speed autoradiography. Temperatures between 17° and −196° C were tested. Early labelling was clearly enhanced by allowing emulsion exposure at low temperatures between −20° to −85° C. Further cooling produced suboptimal labelling and additionally tended to crack the emulsion. Results are shown in Table 1A. At 0.5 microcurie per cc, −85° C was the optimal temperature for labelling.

The effects of scintillator and temperature are most evident with low levels of isotope incorporation and beta emission. By increasing the dose of tritiated thymidine incubated with the cell suspension in vitro to 5–10 microcurie per cc., rapid maximal labelling could readily be accomplished. Results of dose experiments are listed in Tables 1B and 2. With 5–10 microcurie per cc. maximal labelling could be accomplished in 20–60 minutes. Grain counts/cell increased beyond this time, but there was only a negligible increase in the number of cells which become significantly labelled (greater than 5 grains/cell) even extending emulsion exposure to six days. Background label remained low.

Since one major reason for developing this technique was to apply it to the clinical evaluation of patients, samples from a series of patients with leukemias, myeloma, and malignant effusions were obtained. High speed autoradiography with 0.5 – 10 microcurie/cc was compared to standard autoradiography (Coons et al., Cancer, 19, 1200–1204(1966)). Results were entirely comparable in terms of percent cells labelled. From an analysis of duplicate samples for each method a two-fold difference in labelling index was found to be statistically significant ($P<0.05$). Of 52 observations in 40 patients the results of high speed and standard autoradiography had a mean ratio of 1.4 and were therefore not statistically different. Using high speed autoradiography the median labelling index for 11 untreated myeloma patients was 4% and for eight patients in remission 16%. These data were entirely compatible with prior data obtained with standard autoradiography on multiple myeloma patients.

The time necessary to process standard autoradiography has limited many clinical and research applications. This invention provides very short exposure times and facilitates application of autoradiography. It is an improvement over recent modifications of standard autoradiography, including the use of tritiated thymidine (specific activity 6 curies/millimole which gives results in 24–48 hours) and the use of a scintillator along with low specific activity tritiated thymidine.

For low levels of beta emission from incorporated tritiated thymidine, coating of the photographic emulsion with a scintillator greatly enhances early labelling. This effect can be further improved by emulsion exposure at low temperatures, with −85° C being optimal in this invention (table 1A). The method should prove most useful in circumstances in which low levels of isotope uptake have previously required prolonged exposure times (e.g., 6–8 months). We have found that in such procedures with our invention results can be available in 2–3 weeks. There are also potential applications of the invention in electron microscopy, thin layer chromatography and paper chromatography.

A most important modification of the invention is increasing the specific activity of tritiated thymidine to about 40–60 curies per millimole per cc of incubated cells so that maximal cell labelling can be achieved very rapidly. With emulsion exposure times of only 20–60 minutes at 5–10 microcurie per cc, labelling percentages close to maximal are obtained. It is thus possible to calculate labelling index (LI%) or growth fraction within 4–5 hours of obtaining a clinical specimen. The relative labelling intensity or grain count as a function of time may be just as significant as the percentage labelling. It was also possible to rapidly evaluate the rate of labelling by our invention. Therefore in circumstances in which in vitro incubation with high dose high specific activity tritiated thymidine is possible, combined with the use of the scintillator and low temperature exposure (−85° C), data can be made available for rapid clinical decision making. Knowledge of the labelling index is of considerable clinical importance, for example with respect to likelihood of response to chemotherapy in acute leukemia as well as being a marker of response in patients with solid tumors. One major advantage of this method of autoradiography versus other means of rapid cell cycle analysis is the ability to carefully analyze mixed cell populations. With Giemsa staining, and other special stains if desired, cell labelling can be related to conventional morphology and multiple cell populations can be evaluated in a given specimen. The extremely low background observed with this invention appears to be related to the extraordinarily short exposure time required inasmuch as this materially decreases exposure to external environment radiation which is responsible for background.

The methods presented represent a significant advance in the speed with which results can be available from autoradiography. For both research applications which are currently limited by extremely low isotope incorporation rates and in vitro labelling indices for clinical decision making, this invention provides a rapid reliable technique which has wide application in biology and medicine.

TABLE 1

The effect of temperature upon rate of labelling at two different concentrations of tritiated thymidine. Part A was carried out at 0.5 microcurie per cc and 40 – 60 curies per millimole specific activity (s.a.). Part B was carried out at 10 microcuries per cc and same s.a. Results expressed as percent labelled cells (labelling index).

|  | 17° C | | −85° C | |
|---|---|---|---|---|
|  | A | B | A | B |
| 20 minutes | 3 | 29 | 10 | 22 |
| 1 hour | 4.2 | 31 | 11 | 37 |
| 5 hours | 11 | 30 | 19 | 35 |
| 24 hours | 25 | 35 | 27 | 37 |

TABLE 2

The effect of dose of tritiated thymidine upon the rate of labelling, specific activity 40 – 60 curie/millimole. Results expressed as labelling index %.

| μc/cc cells | 0.5 | 2.0 | 5.0 | 10.0 | 50.0 | 100.0 |
|---|---|---|---|---|---|---|
| 20 minutes | 6 | 21 | 26 | 29 | 22 | 25 |
| 1 hour | 21 | 28 | 30 | 31 | 20 | 23 |
| 5 hours | 31 | 44 | 37 | 30 | 34 | 30 |
| 24 hours | 35 | 39 | 36 | 30 | 36 | 29 |
| 6 days | 33 | — | 36 | 35 | 34 | 32 |

DETAILED DESCRIPTION OF THE INVENTION

I. Materials

1. Kodak photographic emulsion — nuclear track NTB3
2. Scintillation fluid: PPO(5 grams) plus dimethyl POPOP (100 mg) dissolved in 500 ml of dioxane.
3. Tween 80 (polyoxyethylene sorbitan monooleate, P1754) used as an emulsifier for photographic emulsion.
4. High-specific activity tritiated thymidine, New England Nuclear NET-027Z; 40–60 curies per millimole
5. Eastman Kodak photographic fixer, Catalog Number 1971746
6. Eastman Kodak D19 developer
7. Giemsa Blood Stain with citric acid buffers, Fisher Scientific Company, G-146, 734319;
8. Other equipment necessary includes an oven and water bath which can be set at 42° C, a dark room, a cytocentrifuge (Shandon), standard glass slides, a 17° C waterbath, slide containers and standard laboratory solutions.

II. Methods

1. For bone marrow samples: Aspirate 2 cc. bone marrow into a syringe containing 0.2 ml. 1/1000 heparin solution (without preservative); mix marrow sample well with heparin. Transfer marrow sample to a culture tube. Add about 3 cc. Hanks solution plus 2 cc. of 3 percent dextran. Work marrow with a 10 ml. pipette. Let marrow separate at 37° at 1 g. for 2 hours. Red cells and granulocytes sediment to the bottom. Take residual white cells and supernatant plasma.
2. Take the pipetted off cells and plasma or previously prepared cell suspension and spin down at 1,200 RPM. Resuspend the cell button and bring up to 10 cc. with Hanks solution.
3. Count the number of cells in the solution with a standard Coulter counter. Resuspend at a concentration of $0.5-1.0 \times 10^6$ cells/cc.
4. Pipette off 2 cc. of suspension into a separate tube. Add 5.0 microcuries per cc. of tritiated thymidine. Incubate for 1 hour at 37° C. Spin and wash two times and resuspend at 0.5–1 million per cc.
5. Make cytocentrifuge slides. For each slide add 3 drops of the prepared cell suspension plus one drop of the Hanks solution. Prepare as many slides as necessary in the cytocentrifuge. Air dry slides.

AUTORADIOGRAPHY

I. Preparation of Reagents and Equipment (In Dark Room)

1. Set oven and waterbath at 42° C.
2. Mix NTB3 nuclear track emulsion with equal volume of distilled water. Add 1.0 ml. of Tween 80 solution. Incubate mixture in 42° C oven for at least 1 hour. Pour 30 ml. of mixture into a plastic container. Place container in 42° C waterbath ready for use.
3. Warm slides on waterbath.
4. Scintillation fluid. Mix 5 grams of PPO plus 100 mg dimethyl POPOP in 500 ml of dioxane. Store in dark bottle.

Procedure

1. Turn off lights in dark room.
2. When NTB3 solution is ready dip each slide one at a time into NTB3 solution for 10 seconds. Prop each slide up to drain and transfer to drying box.
3. Pour the NTB3 solution back into the storage bottle and keep in cold storage.
4. Allow the slides to dry for at least 1 hour.
5. Then dip slides one by one into the scintillation fluid for 10 seconds. Store the slides in a slide box and allow to dry. Keep the slides at room temperature in the dark for 20–60 minutes or longer as required.
6. After exposure period proceed to develop and fix the slides.

DEVELOPMENT AND FIXATION

Preparations

1. Heat 450 ml of distilled water (in 500 ml beaker) on a hot plate to 45° to 50° C. Add the distilled water to the dark jar and bring volume to 500 ml. with cold distilled water until temperature is 37° C (must not vary). Then add 78.5 grams of Kodak D19 developer and stir well. Put in freezer for ½ hour. Place in 17° C waterbath in the dark room.

2. Take 92 grams of the Kodak fixer and dissolve in 350 ml. of distilled water, then bring up to 494 ml. Stir for approximately ½ hour and store in a dark room. Refrigerate for a half hour to bring temperature down to 17° C, then place in the water bath in the dark room.

Procedure

Again with all the lights out pour required volumes of developer and fixer into separate dishes. Place each slide into the developer for 3 minutes then wash in distilled water for 10 seconds. Transfer to the fixing dish for three minutes then transfer each slide to the 17° C water bath where they should stay for 15 minutes. Remove slides from this water bath and allow to air dry. During this period the lights can be turned back on.

STAINING

1. Preparation of the Stain

Dissolve 0.5 grams of Giemsa Blood Stain in 42 ml. of glycerine at 55°–60° C; add 42 ml. methanol and allow to stand 48 hours to complete dissolving. Filter. This is the stock solution. The stain is made in the following way: 75 ml. citric acid (0.1M), buffer pH = 5.75; 5.4 ml. methanol; 4.5 ml. filtered stock stain.

Place stain in first staining dish (100 ml. capacity).

2. Make Up Citric Acid (0.1M) Buffers a. For second staining dish, pH = 5.75; 119.2 ml. of 0.2 M $Na_2HPO_4$, 80.8 ml of 0.1M citric acid, check pH.

b. For third staining dish, pH = 5.40; 111.5 ml. of 0.2 M $Na_2HPO_4$; 88.5 ml. of 0.1M citric acid, check pH.

3. Staining

Dip each slide in the Giemsa blood stain for 12 minutes, then transfer to buffer number 1 which is set at pH 5.75 for 30 seconds, then transfer to buffer number 2 which is set at pH 5.4 for 30 seconds, then allow slide to air dry. The slides are now ready to be coverslipped and counted.

We claim:

1. In a method of measuring physiological changes in tissue which comprises labeling an essential cell constituent with a radioactive isotope by incubating cells with a radiolabeled cell constituent selected from the group consisting of nucleic acids, enzymes, proteins and hormones, which contain a radioisotope as a structural atom thereof, mixing said labeled cells with a liquid scintillator on the surface of a silver halide photographic slide, exposing the silver halide to emissions from the radioisotope, thereby activating silver ions on the slide, developing the slide to produce silver crystals thereon, and determining the relative number of silver crystals as a measure of the radioactivity of the cells and the physiological activity thereof, the improvement wherein the radioactive nucleic acid, enzyme, protein or hormone component each has a specific activity of at least 40 curies per millimole and the silver halide is exposed to the radioactive nucleic acid or enzyme at a temperature not greater than −20° C.

2. The method of claim 1 wherein the radioisotope is tritium.

3. The method of claim 2 wherein the nucleic acid is ribonucleic acid or deoxyribonucleic acid.

4. The method of claim 3 wherein the liquid scintillator is a combination of 2,5-diphenyloxazole and 1,4-bis-(4-methyl-5-phenyloxazol-2-yl)benzene.

5. The method of claim 4 wherein the radioactive nucleic acid component is tritiated thymidine or tritiated uridine.

* * * * *